(12) United States Patent
Shima et al.

(10) Patent No.: US 6,313,325 B1
(45) Date of Patent: Nov. 6, 2001

(54) CARRIER FOR CATALYST FOR USE IN PRODUCTION OF ETHYLENE OXIDE, CATALYST FOR USE IN PRODUCTION OF ETHYLENE OXIDE, AND METHOD FOR PRODUCTION OF ETHYLENE OXIDE

(75) Inventors: Masahide Shima, Kawasaki; Hitoshi Takada, Yokohama, both of (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 09/441,545

(22) Filed: Nov. 16, 1999

(30) Foreign Application Priority Data

Nov. 17, 1998 (JP) .................................................. 10-326516
Jun. 24, 1999 (JP) .................................................. 11-178965

(51) Int. Cl.[7] .................................................. C07D 301/10
(52) U.S. Cl. .................................................. 549/534
(58) Field of Search .................................. 502/347, 348, 502/330, 344, 439, 238, 243, 407, 414, 415, 355; 423/23; 549/534

(56) References Cited

U.S. PATENT DOCUMENTS

| | | | |
|---|---|---|---|
| 4,168,247 | | 9/1979 | Hayden et al. .................. 252/476 |
| 4,212,772 | * | 7/1980 | Mross et al. .................... 252/476 |
| 4,368,144 | * | 1/1983 | Mitsuhata et al. .............. 252/463 |
| 4,389,338 | * | 6/1983 | Mitsuhata et al. .............. 252/463 |
| 4,645,754 | * | 2/1987 | Tamura et al. .................. 502/527 |
| 4,731,350 | * | 3/1988 | Boxhoorn et al. ............... 502/231 |
| 4,740,493 | * | 4/1988 | Boehning et al. ............... 502/348 |
| 4,742,034 | * | 5/1988 | Boxhoorn et al. ............... 502/231 |
| 4,769,358 | * | 9/1988 | Kishimoto et al. .............. 502/348 |
| 4,810,689 | * | 3/1989 | Hayden ........................... 502/347 |
| 4,812,437 | | 3/1989 | Nojiri et al. .................... 502/243 |
| 4,822,900 | * | 4/1989 | Hayden et al. .................. 549/534 |
| 4,829,043 | * | 5/1989 | Boehning et al. ............... 502/348 |
| 4,994,589 | * | 2/1991 | Notermann ..................... 549/534 |
| 5,051,395 | * | 9/1991 | Mitchell et al. ................. 502/348 |
| 5,057,481 | * | 10/1991 | Bhasin ............................. 502/208 |
| 5,063,195 | * | 11/1991 | Jin et al. .......................... 502/341 |
| 5,077,256 | | 12/1991 | Yamamoto et al. ............. 502/243 |
| 5,100,859 | | 3/1992 | Gerdes et al. ................... 502/439 |
| 5,112,795 | * | 5/1992 | Minahan et al. ................ 502/324 |
| 5,380,697 | * | 1/1995 | Matusz et al. ................... 502/348 |
| 5,395,812 | | 3/1995 | Nagase et al. ................... 502/238 |

FOREIGN PATENT DOCUMENTS

| | | | |
|---|---|---|---|
| 0 207 550 | 9/1990 | (EP) | ............................ B01J/23/66 |
| 57-171435 | 10/1982 | (JP) | ............................ B01J/21/12 |
| 4-346835 | 12/1992 | (JP) | ............................ B01J/23/66 |
| 4-363139 | 12/1992 | (JP) | ............................ B01J/23/50 |

* cited by examiner

*Primary Examiner*—Steven P. Griffin
*Assistant Examiner*—Cam N. Nguyen
(74) *Attorney, Agent, or Firm*—Fish & Richardson P.C.

(57) ABSTRACT

A carrier which permits preparation of a catalyst possessed of excellent catalytic performance and used for the production of ethylene oxide, a catalyst obtained by using this carrier, endowed with excellent catalytic performance, and used for the production of ethylene oxide, and a method for the production of ethylene oxide by the use of the catalyst are provided. The carrier is obtained by mixing α-alumina having an alkali metal content in the range of 1–70 m.mols/kg (α-alumina) with an aluminum compound, a silicon compound, and an alkali metal compound and calcining the produced mixture. The carrier which has an aluminum content as reduced to Al in the range of 0–3 mols/kg of carrier, a silicon compound content as reduced to Si in the range of 0.01–2 mols/kg of carrier, and an alkali metal content as reduced to alkali metal in the range of 0.01–2 mols/kg of carrier is used for the deposition of a catalyst for use in the production of ethylene oxide.

16 Claims, No Drawings

CARRIER FOR CATALYST FOR USE IN PRODUCTION OF ETHYLENE OXIDE, CATALYST FOR USE IN PRODUCTION OF ETHYLENE OXIDE, AND METHOD FOR PRODUCTION OF ETHYLENE OXIDE

BACKGROUND OF THE INVENTION

1. Field of the Invention

This invention relates to a carrier to be used in the preparation of a catalyst for use in the production of ethylene oxide, a catalyst obtained by depositing a silver-containing catalytic component on the carrier and used for the production of ethylene oxide, and a method for the production of ethylene oxide by the use of the catalyst.

2. Description of the Related Art

Concerning the catalyst for use in the production of ethylene oxide by gas phase oxidation of ethylene and the carrier therefor, numerous reports have been heretofore introduced to literature.

JP-A-57-171,435, for example, has a description to the effect that a carrier obtained by adding mullite, colloidal silica, etc. to $\alpha$-alumina having a deliberately lowered sodium content has a high specific surface area, a uniform pore distribution, and moreover high wear-resistant properties. EP-B-0,207,550 has a description to the effect that a carrier having a small impurity is obtained by mixing an aluminum compound with the salt of a Group IA metal in the Periodic Table of the Elements and calcining the resultant mixture and a catalyst using this carrier excels in stability. JP-A-04-363,139 discloses a carrier containing $\alpha$-alumina the elements of the fourth, fifth, and sixth periods (such as, for example, titanium, tin, and hafnium) of the IIIa—VIIa and IIIb—Vb groups in the Periodic Table of the Elements and contains a description to the effect that a catalyst using this carrier has high selectivity and a long life. Further, U.S. Pat. No. 5,100,859 discloses a carrier comprising high-purity $\alpha$-alumina, the oxide of an alkaline earth metal, a silicon oxide, and zirconium oxide and contains a description to the effect that a catalyst using this carrier has high initial selectivity and a long life.

We have also proposed a catalyst obtained by depositing silver and cesium as catalytic components on a carrier having a coating layer of amorphous silica disposed on the surface of $\alpha$-alumina and used for the production of ethylene oxide (U.S. Pat. No. 5,077,256) and a catalyst obtained by disposing a coating layer of amorphous silic-alumina on the surface of $\alpha$-alumina and depositing silver and cesium as catalytic components on the resultant carrier and used for the production of ethylene oxide (U.S. Pat. No. 5,395,812).

The catalysts which are disclosed in U.S. Pat. No. 5,077,256 and U.S. Pat. No. 5,395,812 are excellent in catalytic performance and are fully satisfactory from the commercial point of view. Ethylene oxide, however, is produced on a large scale. Even such a small addition to selectivity as 1%, therefore, results in a notable saving in ethylene as a raw material. In the light of the prominence of the economic effect of such an improvement in the selectivity, the desirability of developing a catalyst of more improved performance for the production of ethylene oxide has been finding growing recognition.

An object of this invention, therefore, is to provide a carrier to be used in the preparation of a catalyst for the production of ethylene oxide, a catalyst obtained by depositing silver-containing catalytic component on the carrier and used for the production of ethylene oxide, and a method for the production of ethylene oxide by the use of the catalyst.

Another object of this invention is to provide a carrier which permits preparation of a catalyst possessed of excellent catalytic performance in terms of activity, selectivity, a and used for the production of ethylene oxide, a catalyst obtained by using the carrier just described, endowed with excellent catalytic performance, and used for the production of ethylene oxide, and a method for the production of ethylene oxide by the use of the catalyst just described.

SUMMARY OF THE INVENTION

The objects mentioned above are accomplished by the following items (1)–(8).

(1) A carrier for the catalyst to be used in the production of ethylene oxide, obtained by adding an aluminum compound, a silicon compound, and an alkali metal compound to a low-alkali content $\alpha$-alumina powder having an alkali metal content in the range of 1–70 m.mols/kg of powder and calcining the resultant mixture, the aluminum compound content as reduced to aluminum being in the range of 0–3 mols/kg of carrier, the silicon compound content as reduced to silicon in the range of 0.01–2 mols/kg of carrier, and the alkali metal content as reduced to alkali metal in the range of 0.01–2 mols/kg of carrier respectively in the carrier.

(2) A carrier according to the item (1) mentioned above, wherein the atomic ratio of the alkali metal content in the powder/the alkali metal content in the carrier is in the range of 0.0001–0.8.

(3) A method for the production of a carrier to be used in the production of ethylene oxide, which comprises mixing a low-alkali content $\alpha$-alumina powder having an alkali metal content in the range of 1–70 m.mols/kg of powder with an aluminum compound, a silicon compound, and an alkali metal compound at ratios such that in the produced carrier, the aluminum compound content as reduced to aluminum is in the range of 0–3 mols/kg of carrier, the silicon compound content as reduced to silicon in the range of 0.01–2 mols/kg of carrier, and the alkali metal compound content as reduced to alkali metal in the range of 0.01–2 mols/kg of carrier, forming the resultant mixture in a prescribed shape, and then calcining the formed mixture.

(4) A method according to the item (3) mentioned above, wherein the atomic ratio of the alkali metal content in the powder/the alkali metal content in the carrier is in the range of 0.0001–0.8.

(5) A catalyst to be used in the production of ethylene oxide, obtained by depositing a silver-containing catalytic component on a carrier set forth in the item (1) or the item (2) mentioned above.

(6) A method for the production of a catalyst to be used for the production of ethylene oxide, which comprises depositing a silver-containing catalytic component on a carrier set forth in the item (1) or the item (2) mentioned above and then calcining the resultant composite.

(7) A method according to the item (6) mentioned above, wherein the calcination is effected in the current of an inert gas at a temperature in the range of 400°–700° C.

(8) A method for the production of ethylene oxide, which comprises subjecting ethylene to catalytic gas phase oxidation with a molecular oxygen-containing gas in the presence of a catalyst set forth in the item (5) mentioned above.

The catalyst to be used in the production of ethylene oxide which is obtained by using the carrier of this invention excels in catalytic properties, particularly in selectivity.

DESCRIPTION OF THE PREFERRED EMBODIMENT

The $\alpha$-alumina to be used in this invention must have an alkali metal content in the range of 1–70 m.mols per kg thereof (indicated as "1–70 m.mols/kg of powder" in the present invention). The α-alumina itself does not need to be limited particularly but may be selected from among all the species of α-alumina which are in popular use. The α-alumina which is obtained by the Bayer calcining method, for example, necessarily contains an alkali metal, especially sodium, by reason of the process of manufacture thereof. This invention must use a low-alkali α-alumina which has an alkali metal content thereof controlled in the range of 1–70 m.mols/kg of powder.

If the alkali metal content is less than 1 m.mol/kg of powder or in excess of 70 m.mols/kg of powder, the produced catalyst will manifest too low selectivity for ethylene oxide to accomplish the objects of this invention. The α-alumina which has an alkali metal content in the range of 3–30 m.mols/kg of powder, especially in the range of 5–20 m.mols/kg of powder, is advantageously used.

To be used advantageously in this invention, the α-alumina has an alumina crystal diameter (primary particle diameter) in the range of 0.1–5 μm, an average particle diameter (secondary particle diameter) in the range of 50–100 μm, a BET specific surface area in the range of 1–4 $m^2/g$, and a coefficient of linear contraction due to two hours, calcination at 1700° C. in the range of 12–20%. Incidentally, the expression "coefficient of linear contraction due to two hours' calcination at 1700° C." as used herein means the coefficient of linear contraction which the formed part obtained by pulverizing given α-alumina till the size of α-crystals (primary particles) and forming the crystals under pressure of 1 ton/$cm^2$ exhibits at the end of two hours' calcination at 1700° C.

The carrier of this invention must be obtained by adding an aluminum compound, a silicon compound, and an alkali metal compound generally in combination with an organic binding agent to the low-alkali α-alumina powder mentioned above, molding the resultant mixture in the shape of particles, and then calcining the particles at a temperature in the range of 1200°–2000° C. It is surmised that this calcination operation gives rise to a coating layer of alkali metal-containing amorphous silic-alumina on the- outer surface of α-alumina carrier and the inner surface of the pores thereof.

One of the characteristic features of this invention resides in endowing the α-alumina with such a coating layer of alkali metal-containing amorphous silica or amorphous silic-alumina as described above. The objects of this invention cannot be accomplished by forming a coating layer of amorphous silica or silic-alumina in advance and depositing an alkali metal thereon.

The aluminum compound mentioned above to be effectively used herein has only to be capable of forming an amorphous layer of alkali metal-containing silic-alumina when it is calcined in combination with a silicon compound and an alkali metal compound. As typical examples of the aluminum compound which answers this description, aluminum hydrate, aluminum oxide (γ- or θ-alumina) etc. may be cited. These aluminum compounds may be used either singly or in the form of a mixture of two or more members. The aluminum compound to be used may be a synthetic product or a natural product. Morphologically, the aluminum compound does not need to be particularly discriminated. It may be added in an arbitrary form such as, for example, powder, sol, or aqueous solution. The aluminum compound which is in the form of powder is advantageously used herein when it has a particle diameter in the range of 1–300 nm, preferably in the range of 1–20 nm. Among other forms of aluminum compound, colloidal alumina having a particle diameter in the range of 1–300 nm, preferably in the range of 1–20 nm, is advantageously used. This colloidal alumina is preferred to be used in the form of alumina sol in terms of ease of dispersion. The alumina sol may be obtained by a method of hydrolyzing an aluminum salt or method of neutralizing an aqueous aluminum salt solution with an alkali thereby temporarily gelating the solution and then peptizing the gel, for example.

The silicon compound mentioned above does not need to be particularly discriminated but is only required to be capable of forming an amorphous layer of alkali metal-containing silica or silic-alumina when it is calcined in conjunction with an aluminum compound and an alkali metal compound. As typical examples of the silicon compound which answers this description, silica, feldspar, clay, silicon nitride, silicon carbide, silane, and silicates may be cited. Silic-alumina, aluminosilicates etc. are also usable. These silicon compounds may be used either singly or in the form of a mixture of two or more members. The silicon compound may be a synthetic product or a natural product. Morphologically, the silicon compound does not need to be particularly discriminated. It may be added in an arbitrary form such as, for example, powder, sol, or solution. The silicon compound which is in the form of powder is advantageously used herein when it has a particle diameter in the range of 1–300 nm, preferably in the range of 1–20 nm. Among other forms of silicon compound, colloidal silica having a particle diameter in the range of 1–300 nm, preferably in the range of 1–20 nm, is advantageously used. This colloidal silica is preferred to be used in the form of an aqueous solution in terms of ease of dispersion. The colloidal silica can be obtained by a method of neutralizing an aqueous sodium silicate solution with an acid thereby temporarily gelating the solution and then peptizing the gel or a method of depriving an aqueous sodium silicate solution of sodium by means of ion exchange.

The alkali metal species of the alkali metal compound mentioned above may be any member selected from the group consisting of lithium, sodium, potassium, rubidium, and cesium. Among other alkali metal species mentioned above, potassium and rubidium, particularly potassium, is advantageously used. As typical examples of the alkali metal compound, salts, oxides, hydroxides, etc. of alkali metals may be cited. Since the alkali metal compound in the form of a salt suffers the presence of an anion seed, the anion seed manifests an undesirable effect like a flux during the course of calcination to the extent of rendering difficult the control of physical properties of the carrier. Even after the calcination, the anion seed possibly survives as an impurity and exert an adverse effect on the carrier and, as a consequence, on the performance of the produced catalyst. Among other forms of salt, an organic acid salt which is capable of assuming the form of an oxide at a relatively low temperature is advantageously used. Particularly, the oxides and hydroxides of alkali metals are advantageously used. As typical examples of the oxides and hydroxides of alkali metals, lithium hydroxide, sodium hydroxide, potassium hydroxide, rubidium hydroxide, lithium oxide, sodium oxide, potassium oxide, and rubidium oxide may be cited.

As the organic binding agent mentioned above, any of the organic binding agents which are generally used in the preparation of a carrier for the catalyst to be used for the production of ethylene oxide can be used. As typical examples of the organic binding agent which answers the description, gum arabic, polyvinyl alcohol, hydroxyethyl cellulose, methyl cellulose, carboxymethyl cellulose, and corn starch may be cited. Among other organic binding agents mentioned above, methyl cellulose and corn starch are advantageously used because they produce ash only in a small amount after the calcining operation.

The silicon compound content in the carrier of this invention as reduced to silicon is in the range of 0.01–2 mols per kg of carrier (indicated as "0.01–2 mols/kg of powder" in the present invention). If the silicon compound content is less than 0.01 mol/kg of carrier or in excess of 2 mols/kg of carrier, the catalyst prepared by using this carrier will manifest too low selectivity for ethylene oxide to accomplish the objects of this invention. Properly, the content of the silicon compound in the carrier is in the range of 0.1–1 mol/kg of carrier, preferably in the range of 0.2–0.5 mol/kg of carrier.

The content of the aluminum compound (which originates in the aluminum compound to be added and, therefore, excludes α-alumina) as reduced to aluminum is in the range of 0–3 mols per kg of carrier (indicated as "0–3 mols/kg of carrier" in this invention). If this content exceeds 3 mols/kg of carrier, the catalyst prepared by using this carrier will manifest too low selectivity for ethylene oxide to accomplish the objects of this invention. Properly, the content of the aluminum compound in the carrier is in the range of 0.01–2 mol/kg of carrier, preferably in the range of 0.1–1 mol/kg of carrier.

The content of the alkali metal compound (which originates in the alkali metal compound to be added and, therefore, excludes the alkali metal in the α-alumina) as reduced to alkali metal is in the range of 0.010–2 mols per kg of carrier (indicated as "0.010–2 mols/kg of carrier" in this invention). If the content of the alkali metal compound is less than 0.010 mol/kg of carrier or in excess of 2 mols/kg of carrier, the catalyst prepared by using this carrier exhibits unduly low selectivity for ethylene oxide. Properly, the content of the alkali metal compound in the carrier is in the range of 0.02–0.5 mol/kg of carrier, preferably 0.03–0.3 mol/kg of carrier.

The content of the silicon compound in the carrier, the total content of the aluminum originating in the aluminum compound and the aluminum of the α-alumina, and the total content of the alkali metal originating in the alkali metal compound and the alkali metal in the α-alumina can be calculated from the results of the analysis of composition of the carrier by means of fluorescent X-ray. The aluminum content contemplated by this invention is the total content of aluminum mentioned above minus the amount of the α-alumina to be initially charged and the alkali metal content contemplated by this invention is the total alkali metal content mentioned above minus the aluminum content in the initially charged α-alumina. Thus, the atomic ratio of the alkali metal content in the powder/the alkali metal content in the carrier is generally in the range of 0.0001–0.8, preferably in the range of 0.001–0.5, and more preferably in the range of 0.01–0.3.

The amounts of the aluminum compound, silicon compound, and alkali metal compound to be used relative to the α-alumina during the preparation of the carrier of this invention may be suitably decided so that the contents of aluminum, silicon, and alkali metal in the carrier may fall in the respective ranges mentioned above. The amount of the organic binding agent to be used does not need to be particularly limited but may be properly selected to suit the occasion best.

The method for preparing the carrier of this invention does not need to be particularly restricted. The preparation may be accomplished, for example, by using α-alumina powder as a main aggregate, adding thereto an aluminum compound, a silicon compound, and an alkali metal compound optionally in combination with an organic binding agent, then forming the resultant mixture in a prescribed shape, and calcining the formed mixture at a temperature in the range of 1200°–2000° C. More specifically, the carrier is prepared, for example, by adding an aluminum compound, a silicon compound, an alkali metal compound, and an organic binding agent to α-alumina, optionally further adding water thereto, thoroughly mixing them together by the use of a kneader, granulating the resultant mixture as by extrusion molding, drying the resultant particles, and calcining the dried particles at a temperature in the range of 1200°–2000° C., preferably in the range of 1400°–1800° C., anymore preferably in the range of 1500°–1700° C. Though the extrusion molding is performed in a wet form or a dry form, it is generally performed in the wet form. The drying mentioned above is carried out at a temperature generally in the range of 80°–900° C., preferably in the range of 120°–850° C. Optionally, this drying operation may be omitted.

The order of mixing the α-alumina powder, aluminum compound, silicon compound, alkali metal compound, and organic binding agent does not need to be particularly restricted. It may be properly selected from among such orders as involved in (a) a method which comprises simultaneously mixing these compounds, then forming, drying, and calcining the resultant mixture, (b) a method which comprises mixing the α-alumina with the organic binding agent, drying the produced mixture, then mixing the dried mixture with the aluminum compound, silicon compound, and alkali metal compound, forming, drying, and calcining the resultant mixture, (c) a method which comprises simultaneously mixing the α-alumina, aluminum compound, silicon compound, and organic binding agent, drying the resultant mixture, then mixing the dried mixture with the alkali metal compound, forming, drying, and calcining the resultant mixture, and (d) a method which comprises mixing the α-alumina, alkali metal compound, and organic binding agent, drying the produced mixture, mixing the dried mixture with the aluminum compound and silicon compound, forming, drying, and calcining the resultant mixture.

As a pore forming agent, the powder obtained by pulverizing shells and seeds of peach, apricot, and nut to a uniform particle diameter or a substance having a uniform particle diameter and vanishing in consequence of calcination may be used in combination with the organic binding agent.

Morphologically, the carrier of this invention does not need to be particularly discriminated. Generally, it is used in the form of such particles as spheres, pellets, rings etc. The average equivalent diameter of the particles is generally in the range of 3–20 mm, preferably in the range of 5–10 mm.

The Brunauer-Emmett-Teller (BET) specific surface area of the carrier of this invention is generally in the range of 0.03–10 $m^2/g$, preferably in the range of 0.1–5 $m^2/g$, and more preferably in the range of 0.8–2 $m^2/g$. If the specific surface area is unduly small, the produced carrier will acquire no fully satisfactory water absorption and incur difficulty in retaining the catalytic component fast thereof because it yields to excessive sintering. Conversely, if the specific surface area is unduly large, the pore diameter will be decreased to the extent of suffering the catalyst prepared by using the carrier to promote consecutive oxidation of the ethylene oxide, i.e. the product aimed at. The water absorption of the carrier is generally in the range of 10–70%, preferably in the range of 20–60%, and more preferably in the range of 30–50%. If the water absorption is unduly low, the produced carrier will incur difficulty in retaining the catalytic component fast thereon. If it is unduly high, the produced carrier will fail to acquire fully satisfactory crushing strength. The average pore diameter of the carrier is generally in the range of 0.1–5 μm, preferably in the range of 0.2–3 μm, and more preferably in the range of 0.3–0.9 μm. If the average pore diameter is unduly large, the produced catalyst will suffer degradation of activity. Conversely, if it is unduly small, the carrier will suffer stagnation of gas therein and consequently promote consecutive oxidation of ethylene oxide, the product aimed at. The porosity of the carrier is generally in the range of 40 80%, preferably in the range of 50–70%. If the porosity is unduly low, the produced carrier will acquire an unduly large specific gravity. Conversely, if it is unduly high, the produced carrier will fail to acquire fully satisfactory crushing strength.

The catalyst of this invention to be used for the production of ethylene oxide can be prepared by following the procedure which is generally adopted in the preparation of a catalyst for the production of ethylene oxide while using the carrier described above instead. The catalytic component to be deposited on the carrier may be formed of silver alone or in combination with such a reaction promoting agent as cesium. The expression "depositing a catalytic component" as used in the present invention embraces the mode of depositing silver and a reaction promoting agent in addition to depositing silver alone.

Specifically, the catalyst is produced by preparing a silver compound necessary for the formation of silver either alone or in combination with a complexing agent necessary for the formation of a silver complex and, when necessary, further with an aqueous solution containing a reaction promoting agent, impregnating the carrier with the prepared compound, and then drying and calcining the impregnated carrier. Preferably, this drying is carried out in the air or an oxygen gas or in the atmosphere of an inert gas such as nitrogen gas at a temperature in the range of 80°–120° C. The calcination is preferred to be carried out in the air or an oxygen gas or in the atmosphere of an inert gas such as nitrogen gas at a temperature in the range of 150°–700° C., particularly in the range of 200°–600° C. This calcination may be performed in one stage or in two or more stages. Particularly, the product obtained by performing the first stage in the atmosphere of air at a temperature in the range of 150°–250° C. for a period in the range of 1–10 hours and the second state in the atmosphere of air at a temperature in the range of 250°–450° C. for a period in the range of 0.1–10hours proves preferable for this invention. The product obtained by the procedure which further comprises the third stage to be performed in the atmosphere of an inert gas selected from among nitrogen, helium, and argon at a temperature in the range of 450°–700° C. for a period in the range of 0.1–10 hours proves more preferable.

As typical examples of the silver compound mentioned above, silver nitrate, silver carbonate, silver oxalate, silver acetate, silver propionate, silver lactate, silver citrate, and silver neodecanoate may be cited. As typical examples of the complexing agent, monoethanol amine, diethanol amine, triethanol amine, ethylene diamine, and propylene diamine may be cited. As typical examples of the reaction promoting agent, alkali metals such as lithium, sodium, potassium, rubidium, and cesium and thallium, sulfur, chromium, molybdenum, and tungsten may be cited. These reaction promoting agents may be used either singly or in the form of a mixture of two or more members. The reaction promoting agent is preferred to be an alkali metal, particularly cesium or rubidium.

The catalyst of this invention to be used for the production of ethylene oxide is preferred to deposit thereon silver as a catalytic component and cesium as a reaction promoting agent. The amount of silver to be deposited is generally in the range of 1–30 wt. %, preferably in the range of 5–20 wt. %, based on the weight of the catalyst. The amount of the reaction promoting agent to be deposited is generally in the range of 0.001–2 wt. %, preferably in the range of 0.01–1 wt. %, preferably in the range of 0.1–0.7 wt. %, based on the weight of the catalyst.

The method of this invention for the production of ethylene oxide by the gas phase oxidation of ethylene can be performed by following the procedure which has been heretofore adopted generally for the purpose of the production while using as the catalyst the aforementioned catalyst for the production of ethylene oxide.

Specifically, the production is effected by advancing a feed gas containing of 0.5–40 vol. % of ethylene, 3–10 vol. % of oxygen, 5–30 vol. % of carbon dioxide, and the balance of an inert gas such as nitrogen, argon, or steam and a lower hydrocarbon such as methane or ethane and additionally containing a halide such as ethylene dichloride or diphenyl chloride as a reaction inhibitor at a space velocity in the range of 1000–30000 hr$^{-1}$ (STP), preferably in the range of 3000–8000 hr$^{-1}$ (STP) under a pressure in the range of 2–40 kg/cm$^2$ g, preferably in the range of 15–40 kg/cm$^2$ g, at a temperature in the range of 180°–300° C., preferably in the range of 200°–260° C. into catalytic with the aforementioned catalyst for use in the production of ethylene oxide.

Now, this invention will be described more specifically below with reference to working examples. The word "parts" used therein refers to "parts by weight."

The "degree of conversion" and the "selectivity" mentioned in the working examples and the controls represent the magnitudes calculated respectively by the following formulas.

Degree of conversion (%)=[(Number of mols of ethylene participated in the reaction)/(Number of mols of ethylene contained in the feed gas)]×100

Selectivity (%)=[(Number of mols of ethylene converted into ethylene oxide)/(Number of mols of ethylene participated in the reaction)]×100

EXAMPLE 1

In a kneader, 93 parts by weight of α-alumina powder A (alumina crystal diameter: 1 μm, secondary particle average diameter: 65 μm, BET specific surface area: 2.2 m$^2$/g, coefficient of linear contraction in consequence of two hours, calcination at 1700° C.: 15%, and sodium content 16 m.mols/kg of powder), 6 parts by weight of methyl cellulose, and 6 parts by weight of corn starch were placed and thoroughly mixed and the resultant mixture was thoroughly mixed with 4 parts by weight of colloidal alumina, 2–20 nm in particle diameter, (as Al$_2$O$_3$ content), 3 parts by weight of colloidal silica, 2–20 nm in particle diameter, (made by Nissan Chemicals Industries, Ltd. and sold under the trademark designation of "Snowtex-0") (as SiO$_2$ content), and 0.38 part by weight of an aqueous potassium hydroxide solution (as KOH content) added thereto and20 parts by weight of water further added thereto. A carrier was obtained by extrusion molding the produced mixture, granulating the product of extrusion, drying the granules, and calcining the dried granules at 1450° C. for two hours.

This carrier had a silicon content of 0.5 mol/kg of carrier, an aluminum content of 0.8 mol/kg of carrier, and an alkali metal content of 0.08 mol/kg of carrier and a BET specific surface area of 1.0 m$^2$/g. The atomic ratio of the alkali metal content in the powder/the alkali metal content in the carrier was 0.18.

One liter of the carrier obtained as described was boiled and cleaned in one liter of purified water added thereto under normal pressure at 90° C. for 30 minutes, deprived of the washings, and cleaned with purified water. The boiling and cleaning and the subsequent cleaning mentioned above were repeated twice more and the carrier consequently cleaned was dried at 120° C. for two hours.

The amount, 300 g, of the dried carrier was impregnated with a complex solution consisting of 57.3 g of silver oxalate, 38.6 ml of monoethanolamine, 41.4 ml of water, and 0.18 g of cesium nitrate, then heated and concentrated, further dried at 120° C. for 40 minutes, and then subjected to a heat treatment in a stream of air at 300° C. for 30 minutes to obtain a catalyst (A) for use in the production of ethylene oxide.

EXAMPLE 2

A carrier was obtained by following the procedure of Example 1 while using 0.70 parts by weight of an aqueous rubidium hydroxide solution (as RbOH) in the place of 0.38 parts by weight of the aqueous potassium hydroxide solution.

This carrier had a silicon content of 0.5 mol/kg of carrier, an aluminum content of 0.8 mol/kg of carrier, and an alkali metal content of 0.08 mol/kg of carrier and a BET specific surface area of 0.8 m$^2$/g. The atomic ratio of the alkali metal content in the powder/the alkali metal content in the carrier was 0.18.

A catalyst (B) for use in the production of ethylene oxide was obtained by following the procedure of Example 1 while using the carrier obtained as described above.

EXAMPLE 3

A carrier was obtained by following the procedure of Example 1 while using 0.34 part by weight of an aqueous sodium hydroxide solution (as NaOH) in the place of 0.38 part by weight of the aqueous potassium hydroxide solution.

This carrier had a silicon content of 0.5 mol/kg of carrier, an aluminum content of 0.8 mol/kg of carrier, and an alkali metal content of 0.10 mol/kg of carrier and a BET specific surface area of 0.6 m$^2$/g.

A catalyst (C) for use in the production of ethylene oxide was obtained by following the procedure of Example 1 while using the carrier obtained as described above.

EXAMPLE 4

A carrier was obtained by following the procedure of Example 1 while using 3 parts by weight of carboxy methyl cellulose (0.2 part by weight as Na) and 3 parts by weight of methyl cellulose in the place of 0.38 g of the aqueous potassium hydroxide solution and 6 parts by weight of the methyl cellulose.

This carrier had a silicon content of 0.5 mol/kg of carrier, an aluminum content of 0.8 mol/kg of carrier, and an alkali metal content of 0.10 mol/kg of carrier and a BET specific surface area of 0.6 m$^2$/g.

A catalyst (D) for use in the production of ethylene oxide was obtained by following the procedure of Example 1 while using the carrier obtained as described above.

EXAMPLE 5

A carrier was obtained by following the procedure of Example 1 while using α-alumina powder B (alumina crystal diameter: 3 μm, secondary particle average diameter: 65 μm, BET specific surface area: 0.7 m$^2$/g, coefficient of linear contraction in consequence of two hours' calcination at 1700° C.: 14%, and sodium content: 16 m.mols/kg of powder) in the place of the α-alumina powder A. The atomic ratio of the alkali metal content in the powder/the alkali metal content in the carrier was 0.18.

This carrier had a silicon content of 0.5 mol/kg of carrier, an aluminum content of 0.8 mol/kg of carrier, and an alkali metal content of 0.08 mol/kg of carrier and a BET specific surface area of 0.3 m$^2$/g.

A catalyst (E) for use in the production of ethylene oxide was obtained by following the procedure of Example 1 while using the carrier obtained as described above.

EXAMPLE 6

A carrier was obtained by following the procedure of Example 1 while using α-alumina powder C (alumina crystal diameter: 3 μm, secondary particle average diameter: 65 μm, BET specific surface area: 0.9 m$^2$/g, coefficient of linear contraction in consequence of two hours' calcination at 1700° C.: 15%, and sodium content: 16 m.mols/kg of powder) in the place of the α-alumina powder A.

This carrier had a silicon content of 0.5 mol/kg of carrier, an aluminum content of 0.8 mol/kg of carrier, and an alkali metal content of 0.08 mol/kg of carrier and a BET specific surface area of 0.6 m$^2$/g. The atomic ratio of the alkali metal content in the powder/the alkali metal content in the carrier was 0.18.

A catalyst (F) for use in the production of ethylene oxide was obtained by following the procedure of Example 1 while using the carrier obtained as described above.

EXAMPLE 7

A carrier was obtained by following the procedure of Example 1 while using α-alumina powder D (alumina crystal diameter: 3 μm, secondary particle average diameter: 55 μm, BET specific surface area: 6.0 m$^2$/g, coefficient of linear contraction in consequence of two hours' calcination at 1700° C.: 17%, and sodium content: 16 m.mols/kg of powder) in the place of the α-alumina powder A.

This carrier had a silicon content of 0.5 mol/kg of carrier, an aluminum content of 0.8 mol/kg of carrier, and an alkali metal content of 0.08 mol/kg of carrier and a BET specific surface area of 2.3 m$^2$/g.

A catalyst (G) for use in the production of ethylene oxide was obtained by following the procedure of Example 1 while using the carrier obtained as described above.

EXAMPLE 8

A carrier was obtained by following the procedure of Example 1 while omitting the use of the colloidal alumina.

This carrier had a silicon content of 0.5 mol/kg of carrier, an alkali metal content of 0.08 mol/kg of carrier, and a BET specific surface area of 1.2 m$^2$/g. The atomic ratio of the alkali metal content in the powder/the alkali metal content in the carrier was 0.18.

A catalyst (H) for use in the production of ethylene oxide was obtained by following the procedure of Example 1 while using the carrier obtained as described above.

EXAMPLE 9

A carrier was obtained by following the procedure of Example 1 while using 0.02 part by weight of an aqueous potassium hydroxide solution (as KOH) in the place of 0.38 part by weight of the aqueous potassium hydroxide solution.

This carrier had a silicon content of 0.5 mol/kg of carrier, an aluminum content of 0.8 mol/kg of carrier, and an alkali metal content of 0.02 mol/kg of carrier, and a BET specific surface area of 1.5 m$^2$/g. The atomic ratio of the alkali metal content in the powder/the alkali metal content in the carrier was 0.75.

A catalyst (I) for use in the production of ethylene oxide was obtained by following the procedure of Example 1 while using the carrier obtained as described above.

EXAMPLE 10

A catalyst (J) for use in the production of ethylene oxide was obtained by impregnating 300 g of the carrier obtained in Example 1 with a complex solution comprising 57.3 g of silver oxalate, 38.6 ml of monoethanol amine, 41.4 ml of water, and 0.6 g of cesium nitrate, heating and concentrating the impregnated carrier, further dried at 120° C. for 40 minutes, then subjected to a heat treatment in a stream of air at 300° C. for 30 minutes, and further heat-treated in a stream of nitrogen at 600° C. for 3 hours.

Control 1

A carrier and subsequently a catalyst (K) for use in the production of ethylene oxide were obtained by following the procedure of Example 1 while omitting the use of the aqueous potassium hydroxide solution. The atomic ratio of the alkali metal content in the powder/the alkali metal content in the carrier was 1.0.

Control 2

A complete carrier and subsequently a catalyst (L) for use in the production of ethylene oxide were obtained by following the procedure of Example 1 while using α-alumina powder F (sodium content 0) in the place of the α-aluminum powder A. The atomic ratio of the alkali metal content in the powder/the alkali metal content in the carrier was 0.

Control 3

A carrier was obtained by following the procedure of Example 1 while using α-alumina powder G (alumina crystal diameter: 3 μAm, secondary particle average diameter: 65 μm, BET specific surface area: 2.4 m$^2$/g, coefficient of linear contraction in consequence of 2 hours' calcination at 1700° C.: 17%, and sodium content: 84 m.mols/kg of powder) in the place of the α-alumina powder A.

This carrier had a silicon content of 0.5 mol/kg of carrier, an aluminum content of 3.5 mol/kg of carrier, and an alkali metal content of 0.10 mol/kg of carrier, and a BET specific surface area of 1.3 m$^2$/g.

A catalyst (M) for use in the production of ethylene oxide was obtained by following the procedure of Example 1 while using the carrier obtained as described above.

EXAMPLE 11

The catalysts (A)–(M) were separately pulverized and sifted to separate respective portions of 600–850 mesh. The amount, 1.2 g, of each of the consequently obtained catalyst particles was placed in the reaction tube made of stainless steel which has 3 mm in inside diameter and 600 mm in length, and was used for effecting gas phase oxidation of ethylene under the following conditions. The selectivities and the reaction temperatures of catalyst beds were measured when the ethylene conversion was 10% to obtain results of Table 1.

Space velocity: 6,000 hr$^{-1}$

Reaction pressure: 20 kg/cm$^2$

Feed gas: Composed of 20 vol. % of ethylene, 7.8 vol. % of oxygen, 5.5 vol. % of carbon dioxide, 2.1 ppm of ethylene dichloride, and the balance (methane, nitrogen, argon, and ethane)

EXAMPLE 12

The catalysts (A) and (M) were separately pulverized and sifted to separate respective portions of 600–850 mesh. The amount, 1.2 g, of each of the consequently obtained catalyst particles was placed in the reaction tube made of stainless steel which has 3 mm in inside diameter and 600 mm in length, and was used for effecting gas phase oxidation of ethylene under the following conditions. Selectivities of ethylene oxide and reaction temperatures of the catalyst layers were measured when conversion of ethylene was 25% through whole test duration. The tests were carried out until the yield of ethylene oxide per 1 ml of the catalyst reached to more than 1,000 g. It took more than 25 days to produce 1,000 g of ethylene.

Selectivities of ethylene oxide and reaction temperatures were measured just after conversion of ethylene reached 25% and after 25 days and calculated the differences thereof to obtain results of Table 2.

As being clear from the result that the difference of the calculation is small, it is considered that the catalyst of the present invention is superior in stability of the catalyst performance.

Space velocity: 22,000 hr$^{-1}$

Reaction pressure: 20 kg/cm$^2$

Feed gas: Composed of 20 vol. % of ethylene, 7.8 vol. % of oxygen, 5.5 vol. % of carbon dioxide, 2.1 ppm of ethylene dichloride, and the balance (methane, nitrogen, argon, and ethane)

TABLE 1

| Catalyst used | Selectivity (%) | Reaction temperature (° C.) |
| --- | --- | --- |
| A | 81.4 | 234 |
| B | 81.2 | 236 |
| C | 80.7 | 234 |
| D | 80.7 | 234 |
| E | 81.4 | 236 |
| F | 81.4 | 235 |
| G | 81.4 | 233 |
| H | 80.5 | 236 |
| I | 80.5 | 237 |
| J | 81.4 | 236 |
| K | 80.0 | 240 |
| L | 80.1 | 238 |
| M | 79.2 | 249 |

TABLE 2

| Catalyst | Number of days of reaction | Formed OE (g) | Selectivity (%) | Reaction temperature (° C.) |
| --- | --- | --- | --- | --- |
| Catalyst A | 25 | 1000 | 1.3 | 8 |
| Catalyst M | 25 | 970 | 1.8 | 13 |

The entire disclosure of Japanese Patent Application Nos. 10-326,516 filed on Nov. 17, 1998 and 11-178,965 filed on Jun. 24, 1999 including specification, claims and summary are incorporated therein by reference in its entirely.

What is claimed is:

1. A method for the production of ethylene oxide, characterized by subjecting ethylene to catalytic gas phase oxidation with a molecular oxygen-containing gas in the presence of a catalyst, wherein the catalyst is obtained by depositing a silver-containing catalytic component on a carrier obtained by adding an aluminum compound, a silicon compound, and an alkali metal compound to a low-alkali content α-alumina powder having an alkali metal content in the range of 1–70 m.mols/kg of powder and calcining the resultant mixture, wherein the aluminum compound content as reduced to aluminum being in the range of 0–3 mols/kg of carrier, the silicon compound content as reduced to silicon being in the range of 0.01–2 mols/kg of carrier, and the alkali metal content as reduced to alkali metal being in the range of 0.01–2 mols/kg of carrier, respectively in said carrier.

2. A method according to claim 1, wherein the atomic ratio of said alkali metal content in said powder/said alkali metal content in said carrier is in the range of 0.0001–0.8.

3. A method according to claim 2, wherein said alkali metal content in said α-alumina is in the range of 3–30 m.mol/kg of powder.

4. A method according to claim 2, wherein the secondary particle average diameter of said α-alumina is in the range of 50–100 μm of powder.

5. A method according to claim 2, wherein the BET specific surface area of said α-alumina is in the range of 1–4 $m^2/g$.

6. A method according to claim 2, wherein said aluminum compound content as reduced to aluminum is in the range of 0.01–2 mols/kg of carrier and said alkali metal compound content in the range of 0.02–0.5 mol/kg of carrier in said carrier.

7. A method according to claim 1, wherein said alkali metal content in said α-alumina is in the range of 3–30 m.mol/kg of powder.

8. A method according to claim 7, wherein the secondary particle average diameter of said α-alumina is in the range of 50–100 μm of powder.

9. A method according to claim 7, wherein the BET specific surface area of said α-alumina is in the range of 1–4 $m^2/g$.

10. A method according to claim 7, wherein said aluminum compound content as reduced to aluminum is in the range of 0.01–2 mols/kg of carrier and said alkali metal compound content in the range of 0.02–0.5 mol/kg of carrier in said carrier.

11. A method according to claim 1, wherein the secondary particle average diameter of said α-alumina is in the range of 50–100 μm of powder.

12. A method according to claim 11, wherein the BET specific surface area of said α-alumina is in the range of 1–4 $m^2/g$.

13. A method according to claim 11, wherein said aluminum compound content as reduced to aluminum is in the range of 0.01–2 mols/kg of carrier and said alkali metal compound content in the range of 0.02–0.5 mol/kg of carrier in said carrier.

14. A method according to claim 1, wherein the BET specific surface area of said α-alumina is in the range of 1–4 $m^2/g$.

15. A method according to claim 14, wherein said aluminum compound content as reduced to aluminum is in the range of 0.01–2 mols/kg of carrier and said alkali metal compound content in the range of 0.02–0.5 mol/kg of carrier in said carrier.

16. A method according to claim 1, wherein said aluminum compound content as reduced to aluminum is in the range of 0.01–2 mols/kg of carrier and said alkali metal compound content in the range of 0.02–0.5 mol/kg of carrier in said carrier.

* * * * *